US005760284A

United States Patent [19]

Zoeller

[11] Patent Number: 5,760,284
[45] Date of Patent: Jun. 2, 1998

[54] PROCESS AND CATALYST FOR CARBONYLATING OLEFINS

[75] Inventor: Joseph Robert Zoeller, Kingsport, Tenn.

[73] Assignee: Eastman Chemical Company, Kingsport, Tenn.

[21] Appl. No.: 827,667

[22] Filed: Apr. 10, 1997

[51] Int. Cl.$^6$ ................................................. C07C 67/38
[52] U.S. Cl. ............................ 560/233; 562/521; 562/890
[58] Field of Search ........................... 560/233; 562/521, 562/890

[56] References Cited

U.S. PATENT DOCUMENTS

| | | | |
|---|---|---|---|
| 1,998,218 | 4/1935 | Brown | 260/116 |
| 1,998,219 | 4/1935 | Brown | 260/116 |
| 1,998,220 | 4/1935 | Brown | 260/116 |
| 3,579,551 | 5/1971 | Craddock et al. | 260/413 |
| 3,579,552 | 5/1971 | Craddock et al. | 260/413 |
| 3,790,607 | 2/1974 | Lichstein | 260/408 |
| 3,816,488 | 6/1974 | Craddock et al. | 260/413 |
| 3,816,489 | 6/1974 | Craddock et al. | 260/413 |
| 3,818,060 | 6/1974 | Forster et al. | 260/413 |
| 3,821,265 | 6/1974 | Forster et al. | 260/413 |
| 3,852,346 | 12/1974 | Forster et al. | 260/546 |
| 3,944,604 | 3/1976 | Hershman et al. | 260/533 A |
| 3,946,055 | 3/1976 | Isa et al. | 260/410.9 R |
| 3,980,683 | 9/1976 | Isa et al. | 260/410.9 R |
| 3,989,751 | 11/1976 | Forster et al. | 260/546 |
| 4,323,698 | 4/1982 | Haag | 560/233 |
| 4,335,058 | 6/1982 | Rizkalla | 260/546 |
| 4,354,036 | 10/1982 | Rizkalla | 560/233 |
| 4,372,889 | 2/1983 | Rizkalla | 260/413 |
| 4,407,726 | 10/1983 | Rizkalla | 502/161 |
| 4,483,803 | 11/1984 | Rizkalla | 260/546 |
| 4,537,871 | 8/1985 | Rizkalla | 502/161 |
| 4,540,811 | 9/1985 | Rizkalla | 560/233 |
| 4,558,153 | 12/1985 | Cook | 560/247 |
| 4,625,055 | 11/1986 | Rizkalla | 562/406 |

OTHER PUBLICATIONS

Pino, et al., Organic Syntheses via Metal Carbonyls, Eds. I. Wender and P. Pino, vol. 2, John Wiley & Sons, Inc., New York, NY, pp. 233–296 (1977).

Mullen, New Syntheses with Carbon Monoxide, Ed., J. Falbe, Springer–Verlag, Berlin, Germany, pp. 275–286 (1980).

Colquhoun, et al., Carbonylation—Direct Synthesis of Carbonyl Compounds, Plenum Press, New York, NY, pp. 102–106, 119–130 (1991).

Forster, et al., Catalysis Rev.—Sci. Eng., 23, 89 (1981).

Samel, et al., "Propionic Acid and Derivatives", Ullman's Encyclopedia of Industrial Chemistry, 5th Ed., vol. A22, VCH Publishers, New York, NY, p. 233 (1993).

Bertleff, "Carbonylation", Ullman's Encyclopedia of Industrial Chemistry, 5th Ed., vol. A5, VCH Publishers, New York, NY, p. 223 (1986).

Bittler, et al., Ang. Chem., Int. Ed. 7, 329 (1968).

Tsuji, Organic Synthesis with Palladium Compounds Springer–Verlag, Berlin, Germany, pp. 81–84 (1980).

Imbeaux, et al., J. Chem. Soc., Chem. Comm., 1678–1679 (1992).

Primary Examiner—Michael L. Shippen
Attorney, Agent, or Firm—Michael J. Blake; Harry J. Gwinnell

[57] ABSTRACT

Disclosed is an improved catalyst system and process for preparing aliphatic carbonyl compounds such as aliphatic carboxylic acids, alkyl esters of aliphatic carboxylic acids and anhydrides of aliphatic carboxylic acids by carbonylating olefins in the presence of a catalyst system comprising (1) a first component selected from at least one Group 6 metal, i.e., chromium, molybdenum, and/or tungsten and (2) a second component selected from at least one of certain halides and tertiary and quaternary compounds of a Group 15 element, i.e., nitrogen, phosphorus and/or arsenic, and (3) as a third component, a polar, aprotic solvent. The process employing the improved catalyst system is carried out under carbonylating conditions of pressure and temperature discussed herein. The process constitutes and improvement over known processes since it can be carried out at moderate carbonylation conditions without the necessity of using an expensive noble metal catalyst, volatile, toxic materials such as nickel tetracarbonyl, formic acid or a formate ester. Further, the addition of a polar, aprotic solvent to the catalyst system significantly increases, or accelerates, the rate at which the carbonylation takes place.

15 Claims, No Drawings

PROCESS AND CATALYST FOR CARBONYLATING OLEFINS

This invention was made with United States Government support under Contract No. DE-AC22-94PC94065 awarded by the Department of Energy. The Government has certain rights in this invention.

The inventors in copending application Ser. No. 08/509,039 filed Jul. 28, 1995, describe a process for carbonylating olefins. In particular, that invention sets forth a process for preparing aliphatic carbonyl compounds such as carboxylic acids, esters and anhydrides by contacting carbon monoxide with a mixture comprising an olefin and a catalyst system comprising a Group 6 metal and a halide selected from chlorine, bromine and iodine. The teachings of Ser. No. 08/509,039 are incorporated herein by reference. I have now found that adding a polar, aprotic solvent to the catalyst system can significantly enhance the reaction rates.

BACKGROUND OF THE INVENTION

Carboxylic acids and their anhydrides and esters have a variety of uses in the chemical industry. For example, propionic acid and certain of its salts are used as preservatives in the animal feed and food industries. The anhydrides of propionic and butyric acids are used to manufacture cellulose esters that find a number of uses in the plastics industry.

Acetyl compounds such as acetic acid, acetic anhydride and methyl acetate are manufactured by a very efficient process in which methanol and/or methyl acetate is carbonylated in the presence or absence of water, depending on the desired product. Aliphatic, carboxylic acids containing 8 or more carbon atoms are readily available from natural occurring substances such as natural occurring fats and oils. A need exists for efficient processes for the direct manufacture of aliphatic, carboxylic acids containing 3–9 carbons. At the present time, the major volume of these $C_3$–$C_9$ carboxylic acids are manufactured on a commercial scale by one of 2 methods. This first consists of the sequential hydroformylation and oxidation of olefins as illustrated by equations (1) and (2):

$$R^1CH=CH_2 + CO + H_2 \longrightarrow R^1CH_2CH_2\overset{O}{\overset{\|}{C}}H + R^1CH(CH_3)\overset{O}{\overset{\|}{C}}H \quad (1)$$

$$R^1CH_2CH_2\overset{O}{\overset{\|}{C}}H + R^1CH(CH_3)\overset{O}{\overset{\|}{C}}H + O_2 \longrightarrow$$ (2)

$$R^1CH_2CH_2\overset{O}{\overset{\|}{C}}OH$$

$$+\ R^1CH(CH_3)\overset{O}{\overset{\|}{C}}OH.$$

The second commercial process involves the oxidation of butane or unsaturated natural acids. Derivatives of carboxylic acids require an additional chemical processing step. For example, a propionate ester can be made by esterifying propionic acid with alcohol, using a variety of catalysts known in the art; propionic anhydride can be prepared from propionic acid by an exchange reaction with acetic anhydride.

Hydroxycarbonylation (also referred to as hydrocarboxylation), depicted in equation (3), represents a direct (one step) process for preparing carboxylic acids. More importantly, it offers an advantage in the direct production of derivatives such as esters and anhydrides of the lower carboxylic acids. As exemplified in equations (4) and (5), these processes have the potential to directly generate a carboxylic acid derivative in a single step using an olefin and carbon monoxide, thus eliminating multiple processing steps.

$$R^1CH=CH_2 + CO + H_2O \longrightarrow \quad (3)$$

$$R^1CH_2CH_2\overset{O}{\overset{\|}{C}}OH + R^1CH(CH_3)\overset{O}{\overset{\|}{C}}OH$$

$$R^1CH=CH_2 + CO + MeOH \longrightarrow \quad (4)$$

$$Me=CH_3$$

$$R^1CH_2CH_2\overset{O}{\overset{\|}{C}}OMe$$

$$+\ R^1CH(CH_3)\overset{O}{\overset{\|}{C}}OMe$$

$$2\ R^1CH=CH_2 + 2CO + H_2O \longrightarrow \quad (5)$$

$$\left[ R^1CH_2CH_2\overset{O}{\overset{\|}{C}} \right]_2 O$$

$$+$$

$$\left[ R^1CH(CH_3)\overset{O}{\overset{\|}{C}} \right]_2 O$$

The chemistry involved in equations (3), (4) and (5) is well known, as evidenced by Pino, et al., Organic Syntheses via Metal Carbonyls, Eds. I. Wender and P. Pino, Vol. 2, John Wiley & Sons, Inc.,New York, N.Y., pages 233–296 (1977); Mullen, New Syntheses With Carbon Monoxide, Ed. J. Falbe, Springer-Verlag, Berlin, Germany, pages 275–286 (1980); Colquhoun, et al., Carbonylation—Direct Synthesis of Carbonyl Compounds, Plenum Press New York, N.Y., pages 102–106, 119–130 (1991); and Forster, et al., Catalysis Rev.—Sci. Eng., 23, 89 (1981). However, this chemistry apparently has been used commercially in only a single high pressure, high temperature hydroxycarbonylation unit for the manufacture of propionic acid as the sole product. See Samel, et al., "Propionic Acid and Derivatives", in Ullman's Encyclopedia of Industrial Chemistry, 5th edit., Vol. A22, VCH Publishers, New York, N.Y., page 223 (1993). This propionic acid process uses a highly toxic (and very volatile) $Ni(CO)_4$ catalyst and high pressures (>186 bar, 2700 psi) which requires specialized high pressure equipment. Furthermore, the high temperatures (>270° C.) lead to excessive corrosion and, therefore, require an expensive silver-lined reactor. The operating conditions are more clearly defined in Bertleff, "Carbonylation", in Ullman's Encyclopedia of Industrial Chemistry, 5th edit., Vol. A5, VCH Publishers, New York, N.Y., page 223 (1986).

Processes using moderate pressures and temperatures in the chemistry of equations (3), (4) and (5) are described in the Pino, et al., Mullen, Colquhoun, et al., and Forster, et al. references cited above, in U.S. Pat. Nos. 3,579,551, 3,579, 552, 3,816,488, 3,816,489, 3,818,060, 3,821,265 and 3,852, 346, and in Bittler, et al., Ang. Chem., Int. Ed. 7, 329 (1968) and Tsuji, Organic Synthesis With Palladium Compounds, Springer-Verlag, Berlin, Germany, pages 81–84 (1980).

These processes require an expensive catalyst such as a rhodium, iridium, or palladium catalyst and none has been used on a commercial scale. The propensity of rhodium, iridium, or palladium-based catalysts to precipitate, especially during product separation, is well known, leading to technology to stabilize these catalysts during product separation. Moderate pressure processes using a cobalt-iodide or nickel-iodide catalyst system are described in U.S. Pat. Nos. 3,944,604, 3,989,751, 3,946,055 and 3,980,683.

The carbonylation of olefins in the presence of rhodium-iodide-Group 6 metal and iridium-iodide-Group 6 metal catalyst systems are described in U.S. Pat. No. 3,821,265. Chromium or molybdenum is included in this process to stabilize the rhodium or iridium catalyst complex during distillation.

The preparation of carboxylic acids, esters and anhydrides by the carbonylation of olefins in the presence of a catalyst system comprising (1) a nickel compound, (2) a Group 6 metal, i.e., chromium, molybdenum, or tungsten, (3) a trivalent phosphine, a trivalent amine or an alkali metal, and (4) a halide, e.g., an iodine compound, is described in U.S. Pat. Nos. 4,372,889, 4,407,726, 4,625,055, 4,537,871, 4,335,058, 4,483,803, 4,354,036, 4,540,811. The toxicity of $Ni(CO)_4$, which is likely generated in the system, still represents a problem and a disadvantage.

Systems using a Group 6 metal as the sole metal component have been used to induce carbonylation in substrates other than olefins, and to form esters and acids by adding formate derivatives to olefins. For example, Imbeaux, et al., J. Chem. Soc., Chem. Comm., 1678–1679 (1992) disclose the use of fluoride ions to induce the conversion of alkyl iodides and diiodides to esters and lactones, respectively, using stoichiometric amounts of $Mo(CO)_6$. U.S. Pat. No. 3,790,607 describes a high pressure process for carbonylating fluorocarbon iodides to esters using a series of metal carbonyls including carbonyl compounds of the Group 6 metals. The substrates in both cases are iodides, not olefins, and are used either stoichiometrically or demonstrate limited catalysis.

U.S. Pat. No. 4,558,153 describes the addition of formates to olefins using a catalyst comprising a Group 6 metal, a halide, and optionally, a phosphorus-containing promoter. The source of the carbonyl unit in the process described in that patent is formic acid or a formate ester which must be formed in a separate manufacturing operation. At no point does U.S. Pat. No. 4,558,153 contemplate the addition of carbon monoxide to an olefin to generate the carbonyl unit. In fact, no carbon monoxide is used in most of the examples of the patent.

Finally, the use of Group 6 metal oxides, especially tungsten oxide, formulated as $W_2O_5$, as heterogeneous catalysts for the carbonylation of alcohols is disclosed in U.S. Pat. Nos. 1,998,218, 1,998,219 and 1,998,220. However, the function of the Group 6 metal oxides is to act as strong acids and the reactions were carried out at very high pressures and temperatures, i.e., about 193 bar (2800 psi) and 375° C.

The invention described in Ser. No. 08/509,309 is a process for preparing aliphatic carbonyl compounds such as carboxylic acids, alkyl and aryl esters of carboxylic acids, and anhydrides of carboxylic acids. The catalyst system in that invention contains, as a primary component, a Group 6 metal such as chromium, molybdenum, tungsten, or a mixture thereof and at least one secondary component. I have now found that adding a polar, aprotic solvent to the catalyst system, and using the proper catalyst components and reaction conditions, can significantly enhance reaction rates. The catalyst system and process of the present invention, described in more detail below, are significant improvements over the process set forth in Ser. No. 08/509,039.

DETAILED DESCRIPTION OF THE INVENTION

As stated above, the present invention improves upon the catalyst system and process for carbonylating olefins in Ser. No. 08/509,039 by adding a polar, aprotic solvent to the catalyst system to accelerate the process of forming the carbonylated olefins. Adding just 10 weight % of these materials may accelerate the process by a factor of 2- to 5-fold. Advantages are apparent: smaller reactors, lower catalyst concentrations, and/or lower reaction temperatures.

The present invention sets forth an improved catalyst system and process for generating aliphatic carboxylic acids, esters, and anhydrides by carbonylating olefins. The improved catalyst system of the present invention comprises:

(1) at least one Group 6 metal, such as molybdenum, chromium, tungsten or a mixture thereof;
(2) at least one of:
   (i) a halide selected from the group consisting of chlorine, bromine or iodine;
   (ii) an alkali metal compound;
   (iii) a salt of a quaternary organic compound of an element of Group 15 (such as N and P);
   (iv) a trisubstituted organic compound of an element of Group 15;
   (v) an oxide of a trisubstituted phosphine compound; and
(3) a polar, aprotic solvent, such as a tertiary amide, or oxides of organic sulfides.

The polar, aprotic solvent in the catalyst system of the present invention accelerates the reaction significantly as compared to the process in Ser. No. 08/509,039.

The list of materials generally regarded by organic chemists as constituting the class of polar, aprotic solvents is quite broad. However, useful components include tertiary amides of carboxylic acids, such as dimethyl acetamide and N-methyl pyrrolidinone, tertiary amides of inorganic acids, such as phosphoric acid, or oxides of organic sulfides. Especially useful, based on their availability and ease of handling, are the tertiary amides, particularly dimethyl acetamide and N-methyl pyrrolidinone, and oxides of organic sulfides, such as sulfolane, dimethyl sulfoxide, and dimethyl sulfone. The concentration of the polar aprotic solvent is important in determining the extent of the accelerated effect, but must be balanced with other factors, such as cost of the solvent and its separation. The concentration may range from 1–80 weight %; but a more preferred range is from 2–20 weight %.

Thus, the present invention provides both an improved catalyst system and an improved process for preparing an aliphatic carbonyl compound such as carboxylic acids, alkyl and aryl esters of carboxylic acids, and anhydrides of carboxylic acids. The improved process comprises contacting carbon monoxide with a mixture comprising an olefin and a catalyst system comprising (1) a first component selected from at least one Group 6 metal, i.e., chromium, molybdenum, tungsten, or a mixture thereof and (2) a second component selected from at least one of:

(i) a halide selected from the compounds of chlorine, bromine or iodine;
(ii) an alkali metal compound;
(iii) a salt of a quaternary organic compound of a Group 15 element;

(iv) a trisubstituted organic compound of a Group 15 element; and (v) an oxide of a trisubstituted phosphine compound; and (3) as a third component, a polar, aprotic solvent, under carbonylating conditions of temperature and pressure. The process is preferably carried out in the substantial absence of metals of Groups 8, 9 and 10, (i.e., Fe, Ru, Os, Co, Rh, Ir, Ni, Pd and Pt) and formic acid and formate esters.

Advantages and benefits provided by the invention, in addition to those noted above, include:

(1) eliminating expensive noble metals such as rhodium and iridium; (2) the substantial absence of nickel removes the potential problem of $Ni(CO)_4$ hazards while leading to higher reaction rates; and (3) the expectation that product separation and catalyst recycle will pose fewer problems. Another benefit of the present invention is that neither formic acid nor a formate ester is required to operate the process. Operating the process in the substantial absence of formic acid or a formate ester means that all, or substantially all (e.g., at least 95 mole percent), of the carbonyl units in the resulting carbonyl compounds are obtained from carbon monoxide rather than formic acid or a formate ester.

The first component of the catalyst system above can be any of the Group 6 elements (IUPAC classification), i.e., chromium, molybdenum, tungsten, or a mixture thereof. However, molybdenum is the most active element and, therefore, is preferred. While the Group 6 metal can, in principle, be added as any of a variety of Group 6 metal-containing compounds, molybdenum is generally available in its various oxide forms or as its hexacarbonyl derivative. Molybdenum is best added as a zerovalent metal compound, of which molybdenum hexacarbonyl is the most widely available and lowest cost example.

The catalytically-effective amount of the Group 6 metal can be varied widely but the concentration of the metal in the liquid reaction medium typically will be in the range of about 0.1 mmol to 1 molar with a concentration of about 5 mmol to 500 millimolar being preferred. For the preferred molybdenum system, these molar ranges correspond to weight concentrations of 10 to 96,000 ppm and 50 to 48,000 ppm Mo. Molybdenum concentrations of 1 mmol (96 mg)/L to 100 mmol (9.6 g)/L are particularly useful.

The chloride, bromide, or iodide component can be added in any number of forms such as, for example, an alkyl halide, a hydrogen halide, a salt such as a halide salt of catalyst components (2)(ii) or (2)(iii) defined above, elemental halide, or any combination thereof. The halide component preferably is an iodide; and is best added as the corresponding alkyl iodide, such as ethyl iodide in the case of ethylene carbonylation, or as the hydrogen iodide. When a halide component is present, the atomic ratio of Group 6 metal:X⁻ (wherein X is Cl, Br or I) is about 1:1 to about 1:1000, preferably about 1:1 to 1:100.

Examples of the alkali metal compounds of component (2)(ii) include the halides, especially the iodides, and the alkyl carboxylates of lithium, potassium, rubidium, and/or cesium. Examples of the salts of quaternary organic compounds of a Group 15 element ((2)(iii)), i.e. nitrogen, phosphorus and arsenic, and the trisubstituted organic compound of a Group 15 element ((2)(iv)) include compounds have the general formulas

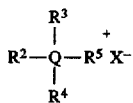

(I)

wherein $R^2$, $R^3$, $R^4$ and $R^5$ are hydrocarbyl groups containing up to about 20 carbon atoms, Q is N, P or As and X is an anion. Because of their availability, the compounds containing nitrogen or phosphorus generally are preferred. Examples of the hydrocarbyl groups are alkyl of up to 20 carbon atoms including aryl substituted alkyl such as benzyl, cycloalkyl of 5 to 7 ring carbon atoms; and aryl such as phenyl and substituted phenyl such as tolyl. Examples of anion X include halogen. The quaternary organic compounds of a Group 15 element and the trisubstituted organic compound of a Group 15 element also may be an amine or a heterocyclic nitrogen-containing compound such as pyridine, quinoline, imidazole, N-methylpyridinium halide, N,N'-dimethylimidazolium halide, and the like; or a bisphosphine compound such as 1,2-bis(diphenylphosphino) ethane.

Examples of the trisubstituted phosphine oxides ((2)(v)) include compounds having the formula

wherein $R^2$, $R^3$, and $R^4$ are defined above. Based on its low volatility and ready availability, trioctylphosphine oxide is particularly preferred. NMR analyses indicates that the use of trisubstituted phosphines of formula (II) in the most active systems results in the in situ conversion of the phosphine to a quaternary phosphonium or phosphine oxide compound.

As stated in Ser. No. 08/509,039, the ratio of the components can vary widely. Acceptable catalytic systems employing, for example, Mo and I may use ratios of Group 6 metal:iodide:copromoter (i.e., copromoter being components 2(ii) through 2(v)) of at least 1:1:0.5 to approximately 1:100:20. Further, the ratio of components may be:

1) Mo:I as being 1:0 to 1:1000, with the preferred range being 1:1 to 1:100, and the Mo:copromoter being defined as from 1:0 to 1:200, with the preferred ratio being about 1:1 to 1:30 and, 2) Mo as being from 0.0001 to 3 molar, with the preferred level being from 0.005 to 0.5M in the initial catalyst solution.

As noted previously, components (2)(i) through (2)(v) may be used individually or in combination. The total amount of components (2)(ii), (2)(iii), (2)(iv) and (2)(v) that may be used range from 1 to 200, preferably 1 to 30 gram atoms [in the case of component (2)(ii)] or moles [in the case of components (2)(iii), (2)(iv) and (2)(v)] per gram atom of Group 6 metal. The optimal combination of secondary catalyst components depends to a great extent on the nature of the olefin reactant, the product being produced, and the resultant design considerations. However, a preferred catalyst system comprises (A) a Group 6 metal, especially molybdenum, (B¹) at least 1 iodine compound, (B²) at least 1 component selected from an alkali metal salt, a salt of a quaternary phosphonium compound, a trisub- stituted phosphine or a trisubstituted phosphine oxide and (c) a polar, aprotic solvent. The iodine compound(s) (B¹) may be provided as the iodide salt of any of the compounds constituting component (B²). However, iodine compound (B¹) more typically is provided as hydrogen iodide and/or an alkyl iodide, e.g., an alkyl iodide containing up to about 8 carbon atoms. When an alkyl iodide is used in the process, it preferably will correspond to the olefin reactant, e.g., ethyl iodide when the olefin reactant is ethylene. Thus, in carbonylating ethylene to produce propionic acid and/or propionic anhydride, a catalyst system consisting essentially of molybdenum as molybdenum hexacarbonyl, iodine as ethyl iodide, tetraalkyl ammonium iodide has been found to possess good to excellent activity and stability.

As the reaction becomes better understood, preferred operating pressures may also be better defined. The reaction is relatively insensitive to the partial pressure of the olefin (such as in the case of ethylene) but inversely dependent upon carbon monoxide until the point at which the catalyst decomposes. Therefore, although Ser. No. 08/509,039 defines the operating ranges of about 8 to 346 bar absolute, with a preferred range of about 18 to 104 bar absolute the preferred range is better defined by the partial pressure of carbon monoxide alone. Thus, the process is operable over a range of 50–1000 psi (3.4–68 atm), but a range of 70–400 psi (5–27.2 atm.) for the carbon monoxide pressure is preferred.

In the case of gaseous olefins, such as ethylene and propylene, although the pressure can range the widely with little effect upon the reaction, it is preferred to match these closely to the stoichiometric amount required. Thus, the partial pressures of the olefins in these cases should closely match the partial pressure of the carbon monoxide component, although this is clearly unnecessary to perform the process of this invention. As previously observed, whereas the process will run in its absence, the inclusion of small amounts of hydrogen has a measurable beneficial effect.

The present carbonylation process generally may be carried out at temperatures in the range of about 75° to 350° C., preferably 140° to 250° C., more preferably 140° to 225° C. and most preferably 140° C. to 200° C. The carbon monoxide may be employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The presence of minor amounts of water such as may be found in the commercial forms of the reactants is, however, entirely acceptable. The gas fed to the carbonylation process preferably comprises carbon monoxide containing up to about 50 volume percent hydrogen. The presence of hydrogen has been found to have a favorable effect on the rate of carbonylation.

Although the olefin can be selected from a long list of ethylenically-unsaturated compounds, e.g. olefins containing from 2 to 20 carbon atoms, there is a limitation inherent in the choice of olefin. For example, the hydroxycarbonylation of higher olefins with the catalyst system described herein introduces a carboxyl or carboxylate group at any one of the carbons along the carbon chain. For example, hydroxycarbonylation of 1-pentene gives mixtures of hexanoic acid, 2-methylvaleric acid, and 2-ethylbutyric acid. A means for controlling the distribution of products for olefins having 5 or more carbons has not yet been discovered. Therefore, the utility of the present carbonylation process for the generation of higher acids ($c_6$ or higher) is limited to systems in which the mixture is either tolerated or preferred. Internal olefins are also useful in this reaction, but again lead to mixtures of products. Thus, the preferred olefin reactants consist of $C_2$–$C_4$ α-olefins, i.e., ethylene, propylene, and the butenes, where there are, at most, only two potential products that are readily separable. Ethylene is the most useful of these olefins.

The process may be operated in a batch, semi-continuous or continuous mode. Hydroxycarbonylation rates can be enhanced dramatically by using production systems designed for very efficient mass transfer, especially when light ($C_2$ to $C_4$) olefins are employed.

As indicated in the above equations a second reaction component, in addition to the olefin and CO, is required to generate product. These are selected from alkyl alcohols or phenols (to form esters), water (to form carboxylic acids), and carboxylic acids (to form carboxylic acid anhydrides). In the case of alcohols and phenols, these can be selected from aliphatic C1–C18 alcohols and C6 through C20 phenolic compounds. More preferred aliphatic alcohols are those having 1 to X (?) carbon atoms, although methanol is the most preferred alcohol. Where a carboxylic acid is used to generate a carboxylic acid anhydride, it is preferred that the carboxylic acid correspond to the acid one carbon higher than the starting olefin. The most preferred example for the conversion of a carboxylic acid to a carboxylic acid anhydride would be generating propionic anhydride from ethylene, propionic acid, and carbon monoxide.

The process may be carried out in the presence of an organic solvent or diluent such as, for example, carboxylic acids and esters, hydrocarbons, e.g., octane, benzene, toluene, xylene and tetralin, or halogenated hydrocarbons such as the chlorobenzenes, e.g., tri-chlorobenzene, or carboxylic acids, or esters such as cellosolve acetate, and the like. In certain instances a material may serve as both solvent and reactant. For example, aliphatic carboxylic acid anhydrides may be prepared by carbonylating an olefin in the presence of a carboxylic acid under substantially anhydrous conditions. In this embodiment of the process, the carboxylic acid functions as both a process solvent and as a reactant. Mixtures of solvents can also be used, such as mixtures of ethyl propionate and propionic acid. The carboxylic acid, when used, should preferably correspond to the acid, or the acid moiety of the anhydride, being produced since the preferred solvent is one that is indigenous to the system, e.g., propionic acid and/or ethyl propionate in the case of ethylene carbonylation. When not a reactant or the product itself, the solvent or diluent preferably has a boiling point sufficiently different from the desired product in the reaction mixture so that it can be readily separated, as will be apparent to persons skilled in the art.

As stated in Ser. No. 08/509,039, the reaction should be run in the presence of a minimum amount of corrosion metals. As demonstrated therein, typical corrosion metals inhibit carbonylation rate. Therefore, as specified above, the carbonylation process is preferably operated in the substantial absence, e.g., less than 300 parts per million (ppm), of the metals of Groups 8, 9 and 10, in general, and nickel and iron, in particular. The inhibition caused by nickel differentiates the present carbonylation process of this invention from the processes described in U.S. Pat. Nos. 4,372,889, 4,407,726, 4,625,055, 4,537,871, 4,335,058, 4,483,803, 4,354,036, 4,540,811 where nickel is the primary component of the catalyst systems disclosed therein.

The most apparent goal of the present invention is to prepare carboxylic acids containing 3 to 9 carbon atoms, preferably carboxylic acids containing 3 to 5 carbon atoms, and most preferably propionic acid, and the anhydride of such carboxylic acids by carbonylating the appropriate olefin. In the manufacture of carboxylic acids, water is included in the carbonylation mixture comprising an olefin, an inert, organic solvent and a catalyst system according to the preceding description. Typically, the amount of water fed to the carbonylation zone is at least 1 mole per mole of olefin and preferably is from 1 to 3 moles of water per mole of olefin. The manufacture of carboxylic anhydrides is carried out under substantially anhydrous condition as is well known in the art. A mixture of carboxylic acids and anhydrides can be produced by carrying out the process in the presence of a limited amount of water.

The present invention may be described by the following examples and comparative examples, which demonstrate the acceleration of the reaction rate due to the polar, aprotic solvent.

EXAMPLE 1

General Procedure. Generating Propionic Anhydride with an N-Methyl Pyrrolidinone Accelerated $Mo(CO)_6$-$Bu_4PI$ Catalyst To allow the measurement of rates, a 2 L Hastelloy® C overhead stirred autoclave was fitted with a high pressure condenser and a dip tube for removing samples during the course of the reaction. Gas mixtures were prepared in a stirred gas mix tank heated to 45°–50° C. and feed lines were heat traced and maintained at 40°–50° C. Failure to keep the mix tank and lines heated often leads to ethylene liquefaction and separation, particularly when cooling begins to occur (due to expansion) as ethylene is either added to the tank during preparation of the gas mixture or as it is removed from the tank during the reaction. The following procedure is exemplary of a typical operation to generate propionic anhydride.

To the autoclave was added 5.81 g (0.022 moles) of $Mo(CO)_6$, 15.5 g (0.040 moles) of tetrabutylphosphonium iodide, 109.2 g (0.700 moles) of ethyl iodide, 555 g (7.5 moles) of propionic acid, and 68.6 g of N-methyl pyrrolidinone (NMP) as polar, aprotic solvent. The condenser temperature is set at 5°–10° C. using a cooled ethylene glycol/water mixture. The autoclave was then pressure tested with nitrogen at 68.0 atm and a gas purge of 3 moles/hr of gas was established through the high pressure condenser. (During the reaction this gas purge permitted control of the gas composition over the reaction mixture and is necessary for kinetic measurements.) The nitrogen was vented, the autoclave was then pressurized to 23.8 atm with 5% hydrogen in carbon monoxide, and subsequently heated to 160° C. (The 3 moles/hr of gas purge is maintained throughout heating and the subsequent reaction.) Upon reaching temperature, the pressure is raised to 51.0 atm using a gas mixture consisting of 6% $H_2$, 47% CO, and 47% ethylene while using the 3 mole/hr purge to maintain the gas mixture. Liquid samples are removed every 20 minutes for 5 hours and analyzed for ethyl iodide, ethyl propionate, propionic anhydride, and propionic acid content by GC using a Hewlett Packard 5890 GC containing a 25 m (0.25 mm ID, 0.25 micron film) Quadrex 007 FFAP Capillary Column with p-xylene as an internal standard. (A split injection was used to introduce the sample and sample detection was accomplished with TCD detector.) These components represented the only significant products and all other materials detectable by GC-MS were only present at trace levels. Gas samples were also removed hourly and analyzed by GC to insure that the gas mixture is consistent. The molar quantities of propionic anhydride (npan) formed were determined from the GC data using the following equation:

$$n_{pan} = \frac{X_{pan}}{130} \cdot \frac{n_{pa}^o + n_{ei}^o}{[(X_{ie}/156) + (X_{pe}/74) + (X_{pan}/130) + (X_{ep}/102)]}$$

where, $n_i$=moles of the component $X_i$=weight fraction of the component (obtained from GC analysis)

$n_{pa}^o$=moles of propionyl initially present =propionic acid added at start $n_{ei}^o$=ethyl iodide initially added Wt=Weight of reaction mixture with subscript designations being:

ep=ethyl propionate pa=propionic acid pan=propionic anhydride ei=ethyl iodide

The molar quantities were plotted against time and the reaction displayed an essentially linear behavior from about 20 minutes into the reaction until the conversion of propionic acid approached about 65–70% where the effects of dilution start to become apparent. (The 20 minute "lag" is not due to an "initiation" period, but represents the time it takes to replace the $H_2$/CO gas mix within the autoclave with the reaction mixture of ethylene/CO/$H_2$.) Therefore, the rate of the reaction (expressed as moles of propionic anhydride formed.kg. of initial reaction solution/hr) was easily determined by using a best fit slope of this plot until either the 5 hr reaction period had expired or the conversion reached 65%. Using this method, the rate of propionic anhydride formation was determined to be 3.4 moles/kg initial solution/hr (440 g.kg initial solution-h).

COMPARATIVE EXAMPLE 1

Generating Propionic Anhydride with an $Mo(CO)_6$-$Bu_4PI$ Catalyst in the Absence of a Polar Aprotic Solvent Example 1 was repeated except the NMP was omitted. The reaction rate was only 1.4 moles/kg initial solution/hr (180 g/kg initial solution-h).

EXAMPLE 2

Generating Propionic Anhydride with a Sulfolane Accelerated $Mo(CO)_6$-$Bu_4PI$ Catalyst Example 1 was repeated except sulfolane was substituted for NMP. The reaction rate was 2.7 moles/kg initial solutions/hr (350 g/kg initial solution-h). This demonstrates the usefulness of a sulfur-based polar, aprotic solvent.

EXAMPLE 3

Generating Propionic Anhydride with an N-Methyl Pyrrolidinone Accelerated $Mo(CO)_6$-$BU_4NI$ Catalyst Example 1 was repeated except tetrabutylammonium iodide was substituted for tetrabutylphosphonium iodide on a molar basis. The reaction rate was 5.4 moles/kg initial solution/hr (700 g/kg initial solution-h).

COMPARATIVE EXAMPLE 2

Generating Propionic Anhydride with an $Mo(CO)_6$-$BU_4PI$ Catalyst in the Absence of a Polar Aprotic Solvent Example 3 was repeated except the NMP was omitted. The reaction rate was only 1.4 moles/kg initial solution/hr (180 g/kg initial solution-h).

EXAMPLE 4

Generating Propionic Anhydride with an N-Methyl Pyrrolidinone Accelerated Mo(CO)$_6$-NaI Catalyst Example 1 was repeated except sodium iodide was substituted for tetrabutylphosphonium iodide on a molar basis. The reaction rate was 2.3 moles/kg initial solution/hr (300 g/kg initial solution-h).

COMPARATIVE EXAMPLE 3

Generating Propionic Anhydride with an Mo(CO)$_6$-NaI Catalyst in the Absence of a Polar Aprotic Solvent Example 4 was repeated except the NMP was omitted. The reaction rate was only 0.8 moles/kg initial solution/hr (100 g/kg initial solution-h).

EXAMPLE 5

Generating Propionic Anhydride with an N-Methyl Pyrrolidinone Accelerated Mo(CO)$_6$-Pyridine Catalyst Example 1 was repeated except pyridine was substituted for tetrabutylphosphonium iodide on a molar basis. The reaction rate was 3.8 moles/kg initial solution/hr (490 g/kg initial solution-h).

COMPARATIVE EXAMPLE 4

Generating Propionic Anhydride with an Mo(CO)$_6$-Pyridine Catalyst in the Absence of a Polar Aprotic Solvent Example 5 was repeated except the NMP was omitted. The reaction rate was only 2.2 moles/kg initial solution/hr (290 g/kg initial solution-h).

The results of the above examples are summarized in Table 1 below.

TABLE 1

Generating Propionic Anhydride from Ethylene, Carbon Monoxide and Propionic Acid in the Presence of Polar Aprotic Solvents

| Example No. | Polar Aprotic Solvent Added | Salt or Group 15 Compound | Rate (mol/kg-h) |
|---|---|---|---|
| 1 | NMP | Bu4PI | 3.4 |
| 1C | None | Bu4PI | 1.4 |
| 2 | Sulfolane | Bu4PI | 2.7 |
| 2C | None | Bu4NI | 1.1 |
| 3 | NMP | Bu4NI | 5.4 |
| 3C | None | NaI | 0.8 |
| 4 | NMP | NaI | 2.3 |
| 4C | None | pyridine | 2.2 |
| 5 | NMP | pyridine | 3.8 |

EXAMPLE 6

Generating Propionic Acid with an N-Methyl Pyrrolidinone Accelerated Mo(CO)$_6$-BU$_4$PI Catalyst The same apparatus and general procedure described in Example 1 for generating propionic anhydride as was used, except the propionic acid was replaced with a mixture of 54 g (4.5 mol) H$_2$O and 510 g (8.5 mol) acetic acid (AcOH). (The AcOH is present as both solvent and internal standard.)

The liquid samples obtained were analyzed for ethyl acetate, ethyl propionate, acetic acid, propionic acid, and water by GC. (The analysis uses the same GC, GC column, and internal standard as Example 1.) Molar quantities of propionyl units generated were calculated by the following equation:

$$np = \frac{[(X_{pa}/74) + (X_{ep}/102] \cdot n_a^o}{[(X_{ea}/88) + (X_{aa}/60)]} \quad [3]$$

where, n=moles

X=weight fraction (obtained from GC analysis)

n$_p$=total moles of propionyl products=E propionic acid+ ethyl propionate n$_a$ $^o$ =moles of acetyl initially present=acetic acid added at start Subscript designations:

ep=ethyl propionate pa=propionic acid ea=ethyl acetate aa=acetic acid

Rates were determined over the span required to consume the entire portion of water added. Using this procedure, the rate of propionic acid generation was found to be 2.2 mol/kg-hr (160 g/kg-h).

COMPARATIVE EXAMPLES 5

Generating Propionic Acid Using a Mo(CO)$_6$-Bu$_4$PI Catalyst in the Absence of a Polar Aprotic Solvent Example 6 was repeated, except that the NMP was omitted. At 160° C., the rate of propionic acid formation was barely detectable and the reaction was repeated at 175° C., where the rate of propionic acid formation was only 0.6 moles/kg-hr (40 g/kg-hr). This clearly demonstrates the ability to use the polar, aprotic solvents to achieve higher reaction rates at lower operating temperatures and further demonstrates that the process may be extended to generate other carboxylic acid derivatives.

The invention has been described in detail with particular reference to preferred embodiments thereof, but it will be understood that variations and modifications can be effected within the spirit and scope of the invention.

I claim:

1. Process for preparing an aliphatic carbonyl compound selected from aliphatic carboxylic acids, alkyl esters of aliphatic carboxylic acids and anhydrides of aliphatic carboxylic acids which comprises contacting carbon monoxide with a mixture comprising an olefin and a catalyst system comprising (1) a first component selected from at least one Group 6 metal and (2) a second component selected from at least one of:

(i) a halide selected from the compounds of chlorine, bromine or iodine;

(ii) an alkali metal compound;

(iii) a salt of a quaternary organic compound of a Group 15 element;

(iv) a trisubstituted organic compound of a Group 15 element; and (v) an oxide of a trisubstituted phosphine compound; and (3) as a third component, a polar, aprotic solvent, under carbonylation conditions of temperature and pressure, wherein the process is carried out in the substantial absence of metals of Groups 8, 9 and 10.

2. Process according to claim 1 wherein the olefin contains 2 to 20 carbon atoms and the carbonylation conditions of temperature and pressure comprise a temperature of about 75° to 350° C. and a carbon monoxide pressure of about 3.4 to 68 atm.

3. A process according to claim 2 wherein the olefin is ethylene, propylene or butene, the temperature is about 140° C. to 225° C., and the carbon monoxide pressure is about 5 to 27.2 atm.

4. A process according to claim 1 wherein the polar, aprotic solvent is a tertiary amide of a carboxylic acid, a tertiary amide of an inorganic acid or an oxide of an organic sulfide.

5. A process according to claim 4 wherein the polar, aprotic solvent is dimethyl acetamide, N-methyl pyrrolidinone, sulfolane, dimethyl sulfoxide or dimethyl sulfone.

6. A process according to claim 2 wherein the second component comprises at least one iodine compound and at least one component selected from a salt of an alkali metal, a salt of a quaternary phosphonium compound, a trisubstituted phosphine or a trisubstituted phosphine oxide, and the olefin contains 2 to 8 carbon atoms.

7. A process according to claim 6 wherein the Group 6 metal is molybdenum.

8. Process for preparing an aliphatic carbonyl compound selected from aliphatic carboxylic acids, alkyl esters of aliphatic carboxylic acids and anhydrides of aliphatic carboxylic acids which comprises contacting carbon monoxide with a mixture comprising an olefin of 2 to 8 carbon atoms, an organic solvent and a catalyst system comprising (1) at least one Group 6 metal, (2) at least one iodine compound and at least one component selected from a salt of an alkali metal, a salt of a quaternary phosphonium compound, a trisubstituted phosphine or a trisubstituted phosphine oxide, and (3) a polar, aprotic solvent wherein the process is carried out at a pressure of about 18 to 104 bar absolute, at a temperature of about 150° to 2500° C., and in the substantial absence of metal of Groups 8, 9 and 10.

9. Process according to claim 8 wherein the organic solvent is an aliphatic carboxylic acid, the olefin contains 2 to 4 carbon atoms, and wherein (1) is molybdenum, and (2) is hydrogen iodide, an alkyl iodide or a mixture thereof, and an iodide salt of an alkali metal, an iodide salt of a quaternary phosphonium compound, a trisubstituted phosphine or a trisubstituted phosphine oxide.

10. Process for preparing propionic acid comprising contacting carbon monoxide with ethylene, water, and a catalyst system comprising (1) molybdenum, (2) hydrogen iodide, an alkyl iodide or a mixture thereof, and an iodide salt of an alkali metal, an iodide salt of a quaternary phosphonium compound, a trisubstituted phosphine or a trisubstituted phosphine oxide, and (3) a polar, aprotic solvent, at a pressure of about 18 to 104 bar absolute, at a temperature of about 150° to 250° C., and in the substantial absence of a metal of Groups 8, 9 and 10.

11. A process according to claim 2 wherein the mixture further comprises water.

12. A process according to claim 2 wherein the mixture further comprises a carboxylic acid.

13. A process according to claim 12 wherein the carboxylic acid is acetic acid, propionic acid or butyric acid.

14. A process according to claim 2 wherein the mixture further comprises an aliphatic alcohol of 1 to 18 carbon atoms or an aromatic alcohol of 6 to 20 carbon atoms.

15. A process according to claim 14 wherein the aliphatic alcohol is methanol.

* * * * *

UNITED STATES PATENT AND TRADEMARK OFFICE
CERTIFICATE OF CORRECTION

PATENT NO. : 5,760,284
DATED : June 2, 1998
INVENTOR(S) : Joseph R. Zoeller

It is certified that error appears in the above-identified patent and that said Letters Patent is hereby corrected as shown below:

Column 14, line 3, delete "2500°C.," and insert therefor ---250°C.,---.

Signed and Sealed this

Twenty-second Day of September, 1998

Attest:

BRUCE LEHMAN

Attesting Officer

Commissioner of Patents and Trademarks